United States Patent [19]

Sepielli

[11] Patent Number: 5,554,894
[45] Date of Patent: Sep. 10, 1996

[54] ELECTRONIC FOOTSWITCH FOR OPHTHALMIC SURGERY

[75] Inventor: Perry Sepielli, Richboro, Pa.

[73] Assignee: Iolab Corporation, Claremont, Calif.

[21] Appl. No.: 330,925

[22] Filed: Oct. 28, 1994

[51] Int. Cl.⁶ .................................................. H01H 35/02
[52] U.S. Cl. ............................ 307/119; 307/112; 604/19;
604/27; 606/32; 606/41; 128/760
[58] Field of Search ..................................... 307/119, 112;
604/19, 27, 317; 128/760; 318/543, 551;
250/221; 606/10, 42, 32, 41

[56] References Cited

U.S. PATENT DOCUMENTS

| | | | |
|---|---|---|---|
| 3,980,849 | 9/1976 | Straihammer | 200/86.5 |
| 4,493,695 | 1/1985 | Cook | 604/27 |
| 4,627,833 | 12/1986 | Cook | 604/34 |
| 4,983,901 | 1/1991 | Lehmer | 318/685 |
| 5,091,656 | 2/1992 | Gahn | 307/119 |
| 5,133,225 | 7/1992 | Lunberg et al. | 74/560 |
| 5,157,603 | 10/1992 | Scheller et al. | 364/413.01 |
| 5,166,513 | 11/1992 | Keenan et al. | 250/221 |
| 5,237,891 | 8/1993 | Neubauer et al. | 74/560 |

OTHER PUBLICATIONS

*Isolab Site Microsurgical*, Johnson & Johnson, Catolog 302-5-125, Copyright 1985, p. 4.
*Site Microsurgical*, Johnson & Johnson, Dec. 1981 Site TXR Catalog, pp. 4 and 7.

Primary Examiner—William M. Shoop, Jr.
Assistant Examiner—Albert Paladini
Attorney, Agent, or Firm—Loeb & Loeb LLP

[57] ABSTRACT

A footswitch for ophthalmic surgery includes a rotatable foot pedal, a spring member which biases the foot pedal to resist rotation and an adjustment mechanism for adjusting the bias of the spring member to a surgeon selected value. In an illustrated embodiment, the adjustment mechanism includes a worm screw gear assembly which is used to vary the amount of torque generated by a coil spring on a shaft upon which a pedal is mounted. As a worm gear is rotated by a thumb wheel, a spur gear is rotated to wind or unwind coil spring thereby increasing or decreasing the amount of tension exerted by coil spring on a shaft.

30 Claims, 4 Drawing Sheets

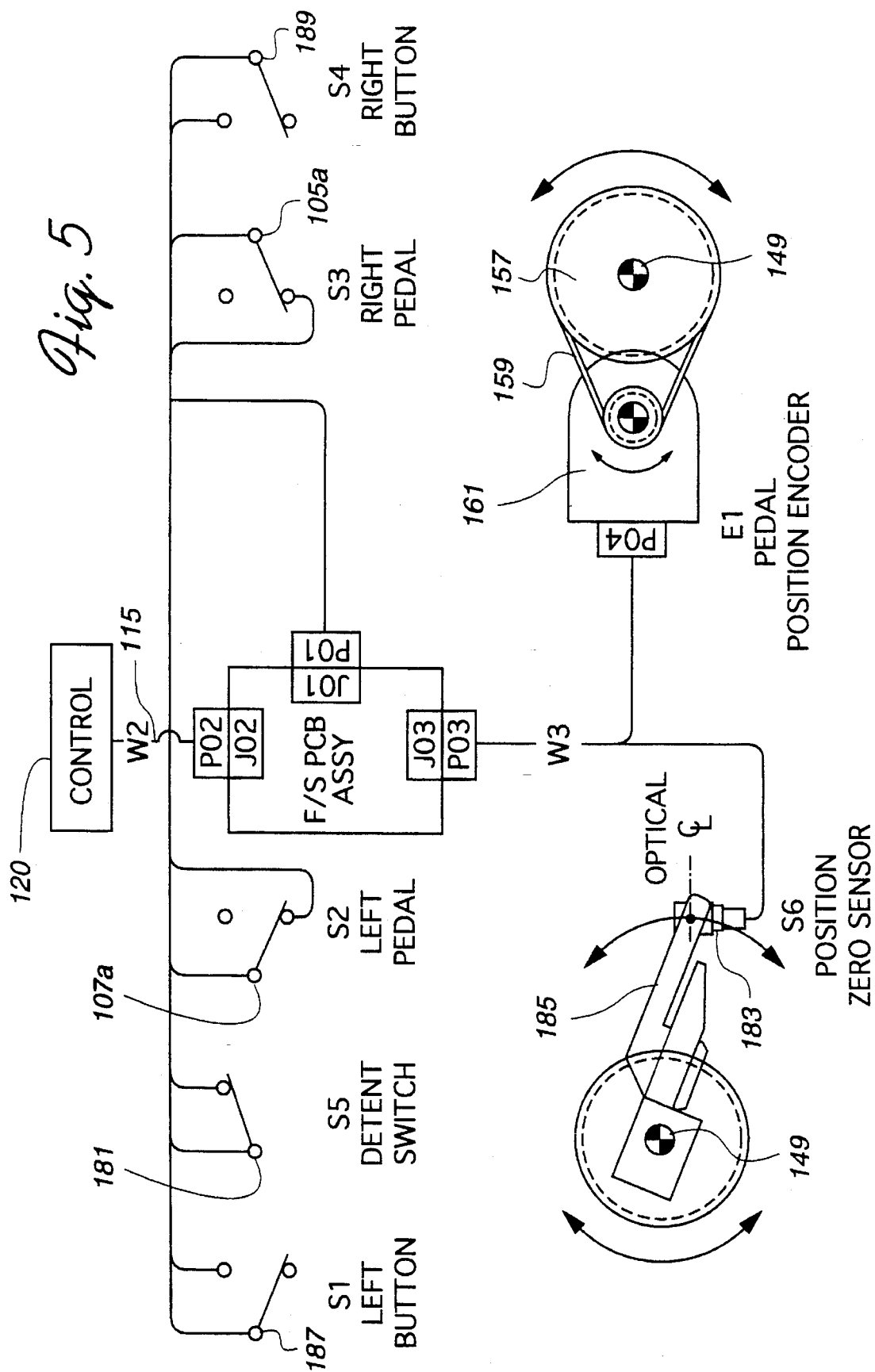

ELECTRONIC FOOTSWITCH FOR OPHTHALMIC SURGERY

FIELD OF THE INVENTION

The present invention relates to the field of ophthalmic surgery, and particularly to a user programmable footswitch for remotely controlling surgical instruments used in ophthalmic surgery.

DESCRIPTION OF THE PRIOR ART

The Prior art microsurgical systems have traditionally involved modular microsurgical components which are integrated into a chassis. These modules may include an inspiration/aspiration (I/A) module, a phaco emulsification module, a microsurgical cutting module, a bipolar coagulating module and a remote illumination module. In these prior art devices, the operation of the respective modules are controlled by one or more footswitches which are connected to the console of the modular system by a vacuum/electrical cable. Vacuum developed by the system is modulated by the footswitch to increase or decrease suction at the tip of the operating instrument from zero to the amount that has been preset on the I/A module.

In one prior art embodiment known as the "dual trigger" footswitch, the footswitch is switchable between a fragmentation mode which is used to control with the phaco emulsification module and handpiece and a cutter mode which is used to control operation of a microsurgical cutting instrument. When the selector is set to fragmentation, and the infusion mode of the infusion/aspiration module is set on auto, depressing the foot pedal to a first position, signaled by an audible click, will activate infusion to the handpiece. Depressing the pedal to a second position, signaled by a second click will activate both infusion and aspiration. Depressing footswitch to a third position will activate infusion, aspiration, and phaco emulsification.

When the selector on the dual-trigger footswitch is set to cut, and the infusion mode is set to auto, the first position will activate infusion, the second position will activate aspiration and pushing a press bar on the right hand side of the foot pedal will activate the microscissors, rotary or guillotine cutting instrument attached to the handpiece.

In this prior art footswitch, control of infusion/aspiration suction is via a pneumatic tubing, while an electrical switch controlled by the sidebar attached to the foot pedal, controls the operation of the microscissors, rotary or guillotine cutter, the phaco emulsification module, and the bipolar module.

U.S. Pat. No. 5,091,656 to Gahn entitled "Footswitch Assembly With Electrically Engaged Detentes" discloses a footswitch apparatus for remote controlling a surgical instrument, and in particular, an ophthalmic microsurgical system. This footswitch also provides a plurality of resistance forces which are staged to provide increasing resistance at predetermined points along the rotational travel of the foot pedal. Thus, the foot pedal provides different tactical feedback for each of the different ranges of operation. This footswitch provides on/off control over irrigation (infusion) and linear foot pedal control over aspiration. This footswitch, together with its associate control system, also provides both fixed and linear control of the phaco emulsification module. The other foot actuated operations available from this footswitch are on/off control.

SUMMARY OF THE INVENTION

The footswitch of the present invention is particularly adapted for use with a single intelligent control console which receives electrical signals from the footswitch to control the various functions of the microsurgical operating system, as selected by the surgeon on a touch-screen display. This touch-screen display provides icons representative of the various functions, i.e., coagulation, phaco emulsification, infusion/aspiration, cutting and illumination. By touching an icon, the surgeon automatically converts the footswitch of the present invention to an operating control for that specific instrument wherein the relative operation of the footswitch varies from function to function. Fixed linear or pulse mode control of the various instruments may be selected by the surgeon, and predetermined preference values may be entered by the surgeon, which are activated by the surgeon during surgery via the footswitch.

The footswitch includes a fixed frame and a foot pedal mounted on a shaft for a pivotal rotation within the frame. One or more spring members are mounted about the shaft and connected to the foot pedal and the frame to bias the foot pedal to a first predetermined position. Means are provided for adjusting the spring bias on the foot pedal to enable the surgeon to select a desired feed back resistance. An electronic encoder is provided for generating an electronic signal representative of the angular rotation of the shaft and the position of the foot pedal. A control means responsive to the electronic encoding means is provided to generate operating signals for a plurality of microsurgical devices, and to vary the operational characteristics of each of said devices in accordance with one or more preset patterns, as determined by the surgeon.

The footswitch also includes selectable detent means which may be switched into engagement with the foot pedal to provide a tactile feedback to the surgeon of various operating ranges of the various microsurgical devices. First and second sideswitches are mounted on the foot pedal to enable the surgeon to control the actuation of various microsurgical devices. In addition, a pair of accessory switches are provided to enable the surgeon to invoke certain preset operating characteristics within the control means.

It is therefore the object of the present invention to provide an improved footswitch for ophthalmic surgery to enable microprocessor control of a plurality of surgical modules, including a phaco emulsification module, a cutter module, bipolar coagulation module and infusion/aspiration module and a fiber optic illumination module.

It is the further object of the present invention to provide an improved footswitch that will cooperate with the control system to provide a plurality of surgeon or user definable functions for each of a plurality of switches provided on the footswitch.

It is the further object of the invention to provide an improved footswitch for ophthalmic surgery which will enable the surgeon to control a variety of surgical procedures with a single footswitch, wherein the tactile feedback from the footswitch remains consistent from procedure to procedure.

It is another object of the present invention to provide a reliable and rugged electronic footswitch for ophthalmic surgery that will provide a consistent tactile feedback to the surgeon over an extended period of use.

It is another object of the present invention to provide a rugged user programmable footswitch with a surgeon definable and adjustable spring bias.

It is another object of the present invention to provide an improved programmable footswitch having an optional surgeon selectable detent mechanism for providing a tactile feedback to the surgery of a plurality of footswitch position.

BRIEF DESCRIPTION OF THE DRAWINGS

FIG. 3a is a partially cross section elevation view of the footswitch illustrated in FIG. 3.

FIG. 5 is diagrammatic view of a wiring harness utilized in the footswitch of the present invention.

DETAILED DESCRIPTION OF THE PREFERRED EMBODIMENT

Figure 1:
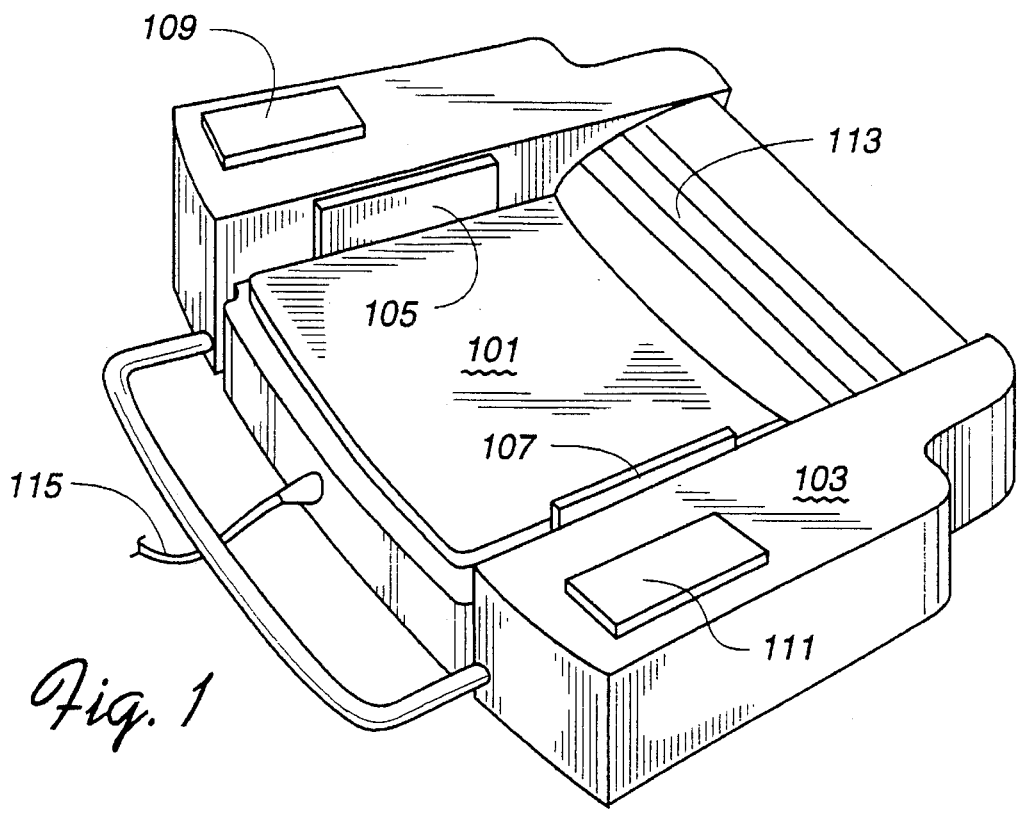
FIG. 1 is an isometric view of the improved electronic footswitch of the present invention.

As illustrated in FIG. 1, the footswitch of the present invention includes a foot pedal 101 which is mounted for pivotal movement on a frame 151 (illustrated in FIG. 3) within housing member 103. The rotatable foot pedal includes first and second sideswitches 105,107 which may be invoked by the surgeon while the foot pedal 101 is depressed. The footswitch of the present invention also includes accessory switches 109,111 which are used to invoke preset patterns or operating characteristics of the surgical instruments, as desired by the surgeon. Housing member 103 also includes a non-slip heel rest 113 to secure the heel against inadvertent slippage. A cable 115 having a multipin connector is provided to connect the footswitch to the control means illustrated in FIG. 2. A guard member 117 protects an electronic connector and its connection to the multipin connector 115 and provides a convenient carrying handle when the switch is being moved.

Figure 2:
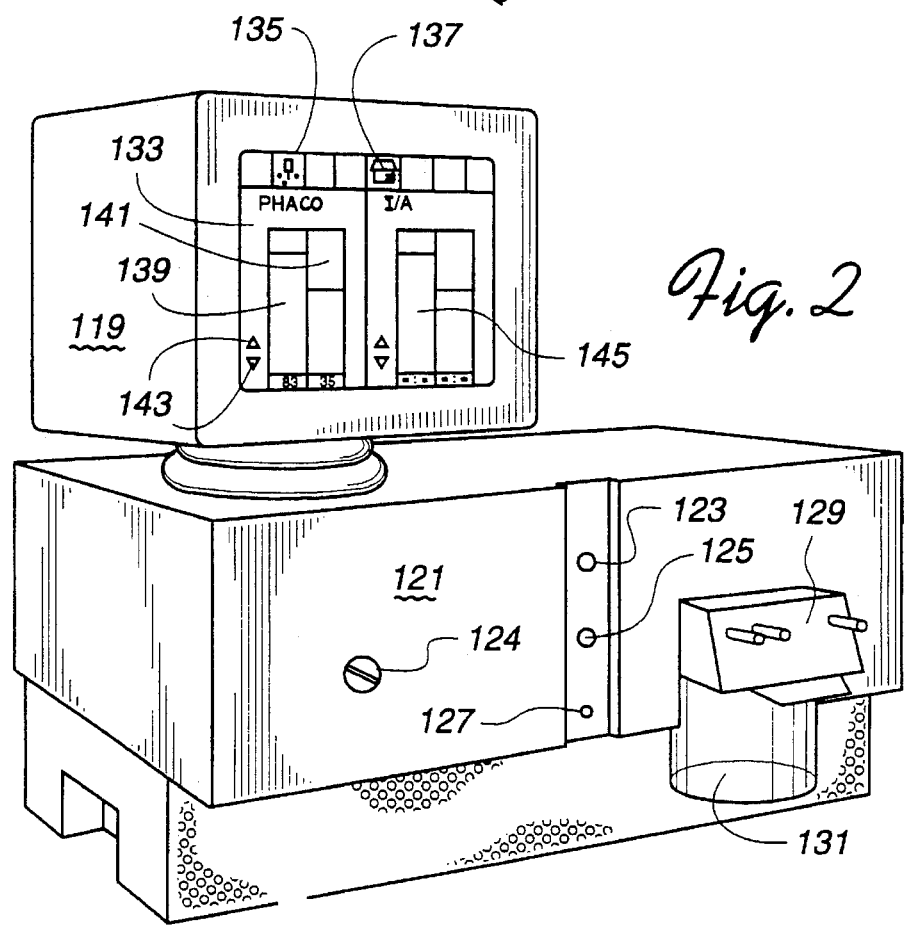
FIG. 2 is an isometric view of the control console and visual display system utilized with the footswitch of the present invention.

FIG. 2 illustrates an automated support system for ophthalmic surgery. This support system includes a control means particularly adapted for use with the footswitch of FIG. 1. This control means is more fully illustrated and described in U.S. Ser. No. 08/330,926, entitled "Control Systems for Ophthalmic Surgery", also assigned to this assignee of the present invention, the disclosure of which is incorporated herein by reference thereto.

The automated control system of the present invention includes a visual display means 119 which may include a CRT display which provides simultaneous visual indications of various variable operating parameters and preset operating parameters as will be hereinafter explained in detail. The automated control system also includes a housing 121 which encloses the computer actuated control system of the present invention, and the various support systems necessary for the operation of the microsurgical devices. Multipin connectors 123–127 are provided on the front of the control system 121 to enable quick and convenient connection of the various microsurgical devices intended for use with the present invention. A replaceable and disposable infusion/aspiration cassette 129 is provided for controlling the flow of an infusion solution, and the aspiration of this solution from the microsurgical site through a plurality of pinch valves and vent chambers defined within the I/A module 129 disposable cassette and an Infusion/Aspiration Suitable module are disclosed in U.S. Pat. Nos. 4,493,695 and 4,627,833, also assigned to the assignee of the present invention. A removable collection container 131 is provided for accumulating fluids and tissues aspirated from the microsurgical site during the surgical procedure.

The visual display means 119 is equipped with a touch-screen 133 for controlling the operation of the automated system. Touch-screen 133 may include a plurality of representational icons such as icon 135 which depicts the end of a phaco emulsifying needle, and fragments of a cataract and icon 137, which illustrates, in graphic section, an infusion/aspiration cassette.

By way of illustrative example, when the surgeon selects icon 135, the control system first determines the presence of a phaco emulsification handpiece at connector 123 and the presence of an infusion/aspiration cassette 129. If both components are present, the control system will retrieve the surgeon's preselected preset power level and display the same on bar graph 139. The surgeon may increase or decrease the preselected power by dragging and dropping the bar graph with his finger on the touch-screen 133, or by incrementing or by de-incrementing the bar graph by touching up/down arrows 143.

During the phaco emulsification procedure, the operation of the foot pedal 101 is as follows. When the foot pedal is at rest, no power is supplied to the handpiece, and bar graph 141 will display 0. As the foot pedal 101 is depressed, the control system will unlock the pinch valve on the infusion line in the I/A module 129 allowing an infusion fluid to flow to the microsurgical site. As the foot pedal 101 is further depressed to a second position, the control system will actuate the I/A module to begin aspiration of infusion fluids from the microsurgical site for deposit in the refuse container 131.

Depending upon the surgeon's preselected preferences, a variety of procedures may then be invoked through the foot pedal depicted in FIG. 1. In one common preset phaco emulsification pattern, as the foot pedal 101 is further depressed, power is applied by the control system to the phaco emulsification handpiece and the bar graph 141 will rise to depict the applied power supplied to the handpiece by the control system. Alternatively, if a fixed or burst mode phaco emulsification pattern is desired, it may be initiated with the right side switch 105, while the aspiration vacuum level is controlled by varying the vacuum pump speed by varying the rotational position of foot pedal 101. If this mode is selected, a second set of bar graphs will be depicted on the touch-screen 133, in which bar graph 145 depicts a preset maximum aspiration vacuum level i.e., 450 mmHg. The second bar graph will depict the actual aspiration vacuum, which may be varied by the surgeon by rotating foot pedal 101 downwardly. In this mode of operation, the second sideswitch 107 may be used as a reflux switch to evacuate the collection container 131 by reversing the vacuum pump and applying the positive pressure to the collection chamber. In this procedure, accessory buttons 109,111 may also be used to set other surgical values or actuate other surgical procedures. For instance, the surgeon may select one phaco emulsification power for a Class 3 cataract, and a second phaco emulsification power for a Class 4 cataract. By simply tapping the accessory switch 109, the preset power can be increased to a second preset value, when desired by the surgeon.

The foregoing illustration is by way of illustrative example, and similar preset pattern and configurable surgeon preferences may be set for cutting or coagulation, wherein the selection of an icon on the touch-screen 133 will invoke the cutting procedure or the coagulation procedure as desired. Depending upon the procedure selected, the foot pedal 101 and footswitches 105–111 may be preset to control a variety of operating parameters, as determined by the surgeon.

Figure 3:
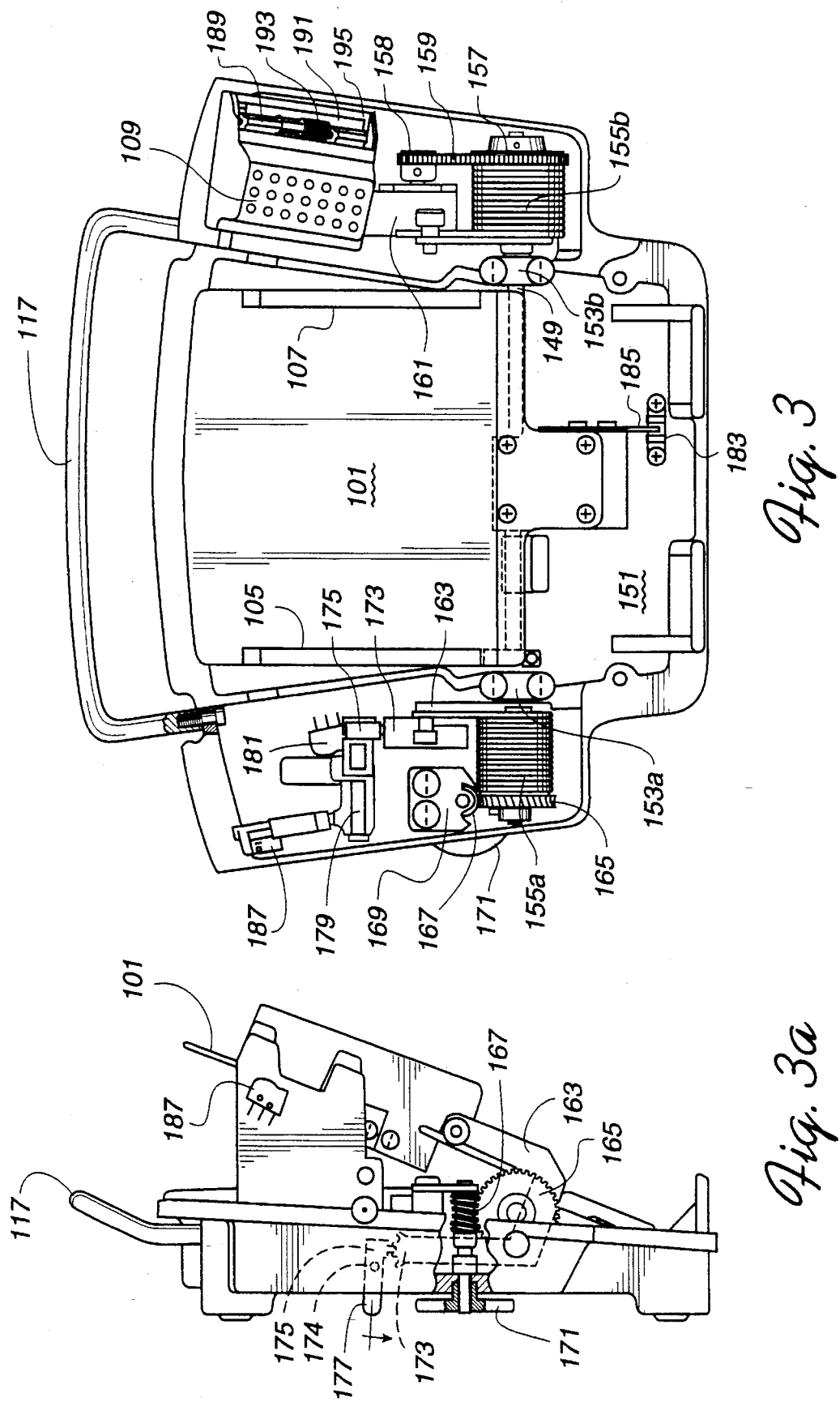
FIG. 3 is a partially cross sectioned planned view of the footswitch with the housing removed.

The mechanical construction of the footswitch is depicted in FIGS. 3–6 wherein FIG. 3 is a partially cross-sectioned plan view of the footswitch with the housing removed, and FIG. 3(a) is a partially cross-sectioned elevation view of the left side of the footswitch as illustrated in FIG. 3.

As illustrated in FIG. 3, the foot pedal 101 is mounted on shaft 149 for pivotable movement within the housing and with respect to frame 151. The foot pedal as mounted on shaft 149, which is journaled for rotation within bearings 153(a),(b) and is biased to a first predetermined position illustrated in FIG. 3(a) by a pair of coil springs 155(a), 155(b). At the end of shaft 149 is a toothed gear 157 which drives a toothed belt 159 to rotate a reduction gear 158 and an opticalencoder 161. The drive ratio between gear 157 and the optical encoder 161 is increased to amplify the rotational movement of the foot pedal 101 with respect to the encoder to thereby achieve greater positional accuracy. The optical encoder 161 is used to generate electronic signals for the control means of the present invention to enable the control means to determine the angular position of foot pedal 101.

The pedal 101 is biased upwardly by a pair of coilsprings 155(a) and 155(b), one of which is provided with an adjustable biasing means. The other hand of the coil spring is secured to a worm screw gear assembly 165, 167 which is used to vary the amount of torque generated by the coil spring 155(a) on shaft 149. The worm drive screw 167 is mounted to the frame member 151 by means of bracket 169 and as the worm gear 167 is rotated by thumb wheel 171, the spur gear 165 is rotated to wind or unwind coilspring 155a thereby increasing or decreasing the amount of tension exerted by coil spring 155(a) on shaft 149. The use of a worm screw gear assembly prevent the spring tension in coil 155a from unwinding the drive screw 167 and altering the designed spring bias. Pedal tension is nominally set at 4 pounds pressure, but it can be manually adjusted by the surgeon to approximately 6 pounds of pressure by rotating the knurled wheel 171 which is located at the side and bottom of the footswitch. Tension setting indicates (0–5) may be added to assist the surgeon selecting a desired value.

Affixed to the outer end of arm 163 is a cam member 173 which has a plurality of detent surfaces formed therein that are engaged by a movable detent means 175. Detent means 175 is pivoted for reciprocal movement about pivitpin 174 into and out of engagement with cam 173 in response to movement of lever 177, as illustrated in FIG. 3(a). A second detent means 179 is used to secure the first detent means 175 in one of two positions. The first position is a retracted position, out of engagement with the cam member 173, when the lever 177 is thrown to the second position detent 179 holds the detent means 175 in engagement with cam surface 173. A microswitch 181 is provided to provide electronic feedback to the control system when the detent mechanism 175 is engaged. The purpose of the detent mechanism 175 and the cam member 173 is to provide a tactual feedback at preselected angular orientations of foot pedal 101 so that the surgeon may know that the angular orientation of the foot pedal 101 is ready to begin the next surgical procedure. If the tactual feedback is not desired, the detent means 175 may be snapped out of engagement by throwing lever 177 in the direction of arrow "a" as illustrated in FIG. 3(a).

An optical switch 183 is positioned at the heel of the foot pedal to provide a zero point and reset reference for the control system of the present invention. The optical switch 183 is actuated by a flag 185 attached to the heel portion of foot pedal 101. Thus, whenever the foot pedal is returned to its original starting position, the optical switch 193 will generate a reset signal for the control means of the present invention.

Also illustrated in FIG. 3 is an accessory switch 187, which is mounted on the upper portion of frame member 151 in a normally open position. For the purposes of illustrative convenience, the accessory button 111 for switch 187 has been omitted in FIG. 3(a), but the actuating button 109, and its associated microswitch 189 are illustrated in FIG. 3. Both of the accessory switch buttons 109,111 are pivotably mounted on shaft members, one of which is illustrated at 191 is FIG. 3. The accessory button 109 is normally biased upwardly by coil spring 193 to cause an actuating arm 195 to engage the microswitch 189 when microswitch 189 is thus engaged, the microswitch 189 is open. As the accessory button 109 is depressed, the actuating bar 195 is lifted, allowing microswitch 189 to close.

As indicated previously, microswitches 187,189 may be used by the surgeon to preset a variety of desired operating ranges for microsurgery, the functions of which may be varied depending upon which surgical procedure is selected.

Figure 4:
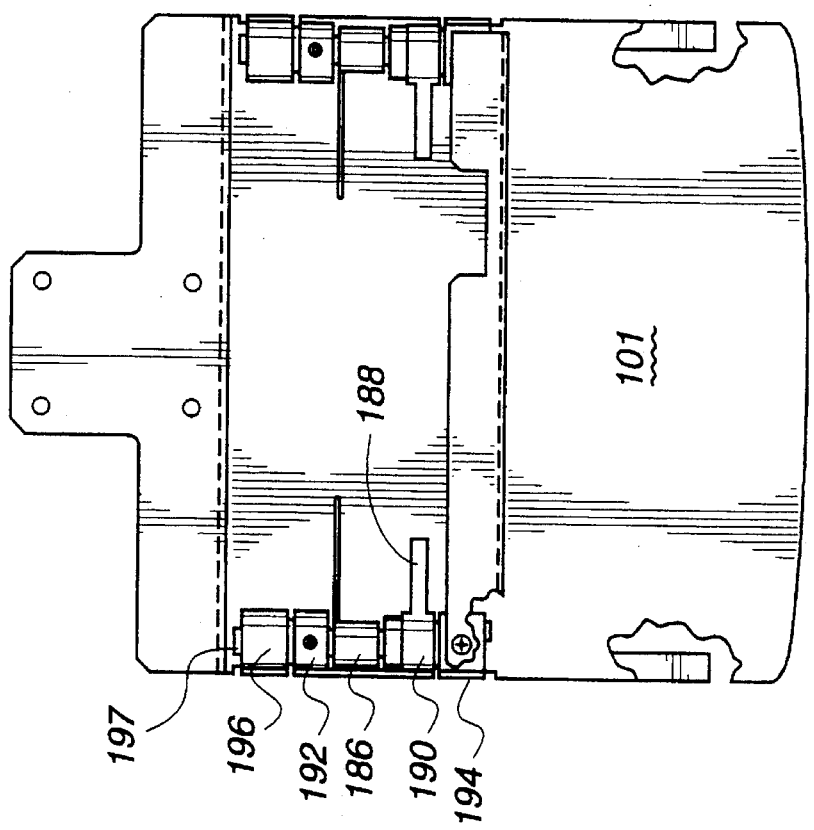
FIG. 4 is a planned view of the underside of the foot pedal utilized in the footswitch of the present invention.
Figure 4A:
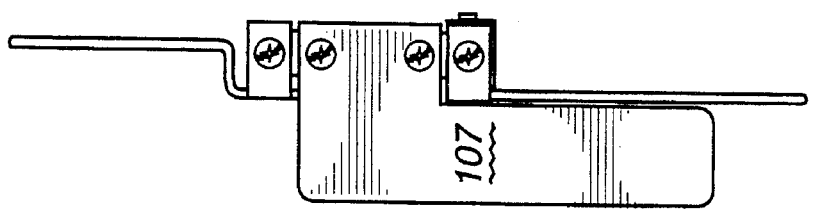
FIG. 4a is an elevation view of the foot pedal illustrated in FIG. 4.

Side switches 105,107 are mounted for pivotal movement on foot pedal 101, as more fully illustrated in FIGS. 4 and 4(a). As illustrated in FIG. 4, foot pedal 101 is illustrated from below. Side switch 107 is illustrated in corresponding elevation in FIG. 4(a). Side switch 107 is mounted for rotation about a shaft member 197 which is secured to the foot pedal 101 by fixed bosses 194,196. The side switch 107 is joined for rotation to pivots about shaft member 197 on joined bearing members 190,192. An arm member 188 is fixably mounted on moveable bearing member 190 to rotate about shaft 197 when the side switch 107 is rotated outwardly. When sideswitch 107 is rotated outwardly, or laterally with respect to the foot pedal, arm member 188 is rotated towards the underside of pedal 101. An electrical microswitch (not shown in FIG. 4) for side switch 107 is mounted on arm 188, and is thus reciprocated into engagement with the foot pedal 101 and actuated whenever the side switch 107 is displaced outwardly from the upper surface of foot pedal 101. The foot pedal 107 is biased to its inward position as illustrated in FIG. 1 by virtue of a coil spring 186 which engages both foot pedal 101 and the side switch 107. Side switch 105 is similarly mounted to the opposite side of foot pedal 101 with the same construction and biasing arrangement described and illustrated with respect to side switch 107.

FIG. 5 illustrates a wiring harness for the foot switch and the home position of each of the switches hereinbefore described in detail. As illustrated in FIG. 5, the rotation of shaft 149 will lift flag 185, thereby closing the optical switch 183, which generates a signal for the control means 120 that pedal rotation has begun. This signal is a start mark for the optical encoder 161 which then generates a plurality of electronic pulses for each degree of rotational movement of shaft 149, as foot pedal 141 is depressed. As illustrated in FIG. 5, the upper accessory buttons 109,111 which actuate microswitches 187,189 are normally opened and closed by depressing buttons 109,111. Detent switch 181 provides a signal to the control means 120 that the detent has been engaged. Microswitches 105(a) and 107(a) are actuated by right and left pedal switches 105,107 and are normally closed. The wiring harness illustrated in FIG. 5 is connected to the control means 120 by virtue of a cable 115 and a multipin connector.

While a preferred embodiment of the present invention has been disclosed and described herein, it should be understood that the invention is not limited to such embodiment, but rather it is intended to include all the embodiments which would be apparent to one skilled in the art which come within the spirit and scope of the following claims.

I claim:

1. An electronic footswitch for use in controlling a plurality of surgical devices used by a surgeon in ophthalmic surgery, said footswitch comprising:
   (a) a fixed frame and housing;
   (b) a shaft and a foot pedal mounted on the shaft for pivotable rotation with respect to said frame, said shaft being journaled for rotation within said housing;
   (c) a spring member mounted about said shaft and coupled to said foot pedal and to said housing to bias said foot pedal to resist rotation of the foot pedal;
   (d) continuously adjustable means coupled to the spring member for adjusting the bias of said spring member to a surgeon selected value;
   (e) electronic encoding means for generating an electronic signal representative of the rotation of said shaft;
   (f) control means responsive to said electronic encoding means and said plurality of surgical devices, to vary a plurality of operational characteristics of said devices in accordance with preset patterns set by said surgeon.

2. An electronic footswitch as claimed in claim 1, wherein at least one of said surgical devices has a plurality of operating ranges associated therewith, and said apparatus further comprises surgeon selectable detent means for providing a tactile feedback to a surgeon as the foot pedal rotates, said feedback providing an indication of an associated operating range.

3. An electronic footswitch for use in controlling a plurality of surgical devices used by a surgeon in ophthalmic surgery, said footswitch comprising:
   (a) a fixed frame and housing;
   (b) a shaft and a foot pedal mounted on the shaft for pivotable rotation with respect to said frame, said shaft being journaled for rotation within said housing;
   (c) a spring member mounted about said shaft and coupled to said foot pedal and to said housing to bias said foot pedal to a first predetermined position;
   (d) continuously adjustable means for adjusting the bias of said spring member to a surgeon selected value;
   (e) electronic encoding means for generating an electronic signal representative of the rotation of said shaft;
   (f) control means responsive to said electronic encoding means and said plurality of surgical devices, to vary a plurality of operational characteristics of said devices in accordance with preset patterns set by said surgeon: and
   wherein said apparatus further comprises first and second foot actuable switches mounted at the sides of said foot pedal, said side switches being coupled to said control means to activate one or more surgical devices.

4. An electronic footswitch as claimed in claim 3, wherein at least one of said surgical devices has a surgeon preset range associated therewith, and said apparatus further comprises at least a third foot actuable foot switch coupled to said control means to enable a surgeon to invoke a surgeon preset range for said at least one surgical device.

5. An electronic footswitch as claimed in claim 1, wherein said spring member is a single coil spring coaxially mounted around said shaft, said coil spring exerting a preset bias on said foot pedal.

6. An electronic footswitch as claimed in claim 5, wherein said continuously adjustable means is mounted between said frame and said coil spring, and varies the rotational torque exerted by said spring on said shaft.

7. An electronic footswitch for use in controlling a plurality of surgical devices used by a surgeon in ophthalmic surgery, said footswitch comprising:
   (a) a fixed frame and housing:
   (b) a shaft and a foot pedal mounted on the shaft for pivotable rotation with respect to said frame, said shaft being journaled for rotation within said housing;
   (c) a spring member mounted about said shaft and coupled to said foot pedal and to said housing to bias said foot pedal to a first predetermined position;
   (d) continuously adjustable means for adjusting the bias of said spring member to a surgeon selected value;
   (e) electronic encoding means for generating an electronic signal representative of the rotation of said shaft;
   (f) control means responsive to said electronic encoding means and said plurality of surgical devices, to vary a plurality of operational characteristics of said devices in accordance with preset patterns set by said surgeon;
   (g) wherein said spring member is a single coil spring coaxially mounted around said shaft member, said coil spring exerting a preset bias on said foot pedal:
   (h) wherein said continuously adjustable means is mounted between said frame and said coil spring, and varies the rotational torgue exerted by said spring on said shaft; and
   wherein said continuously adjustable means includes a rotatable screw member which varies the preload on said coil spring as it is rotated by the surgeon.

8. An electronic footswitch for use in controlling a plurality of surgical devices used by a surgeon in ophthalmic surgery, said footswitch comprising;
   (a) a fixed frame and housing;
   (b) a shaft and a foot pedal mounted on the shaft for pivotable rotation with respect to said frame, said shaft being journaled for rotation within said housing;
   (c) a spring member mounted about said shaft and coupled to said foot pedal and to said housing to bias said foot pedal to a first predetermined position;
   (d) continuously adjustable means for adjusting the bias of said spring member to a surgeon selected value;
   (e) electronic encoding means for generating an electronic signal representative of the rotation of said shaft;
   (f) control means responsive to said electronic encoding means and said plurality of surgical devices, to vary a plurality of operational characteristics of said devices in accordance with preset patterns set by said surgeon
   (g) wherein said apparatus comprises surgeon selectable detent means which provide a tactile feedback to a surgeon as the foot pedal travels through a plurality of operating ranges for said surgical devices; and
   wherein said apparatus further comprises a cam member mounted on said shaft, said cam member having a plurality of surfaces thereon which may be engaged by said detent means to provide said tactile feedback to the surgeon.

9. An electronic footswitch as claimed in claim 8, wherein said detent means is mounted for reciprocal movement between first and second positions, with said first position in engagement with said cam, and a second position out of engagement with said cam.

10. An electronic footswitch as claimed in claim 1, wherein said control means varies the speed of a first surgical device in response to rotation of said footpedal, and varies the speed of a second device when a footpedal side switch is actuated.

11. An electronic footswitch for use in controlling a plurality of surgical devices having a plurality of operational characteristics within surgeon defined preset patterns of operations, when used by a surgeon in ophthalmic surgery, said footswitch comprising:

(a) a supporting member, a shaft and a foot pedal mounted on the shaft for pivotable rotation about a first axis, said shaft being journaled for rotation within the support member;

(b) first and second side switches mounted on said foot pedal for independent activation of one or more surgical devices throughout the range of motion of said foot pedal;

(c) a spring member mounted about said shaft and coupled to said foot pedal and to said support member to resist rotation of the foot pedal;

(d) continuously adjustable means for adjusting the bias of said spring member to a surgeon selected value;

(e) electronic encoding means for generating an electronic signal representative of the rotation of said shaft;

(f) control means responsive to said electronic encoding means and said plurality of surgical devices, to vary a plurality of operational characteristics of said devices in accordance with preset patterns set by said surgeon.

12. An electronic footswitch for use in controlling a plurality of surgical devices having a plurality of operational characteristics within surgeon defined preset patterns of operations, when used by a surgeon in ophthalmic surgery, said footswitch comprising:

(a) a supporting member, a shaft and a foot pedal mounted on the shaft for pivotable rotation about a first axis said shaft being journaled for rotation within the support member:

(b) first and second side switches mounted on said foot pedal for independent activation of one or more surgical devices throughout the range of motion of said foot pedal:

(c) a spring member mounted about said shaft and coupled to said foot pedal and to said support member to bias said foot pedal to a first predetermined position;

(d) continuously adjustable means for adjusting the bias of said spring member to a surgeon selected value:

(e) electronic encoding means for generating an electronic signal representative of the rotation of said shaft:

(f) control means responsive to said electronic encoding means and said plurality of surgical devices, to vary a plurality of operational characteristics of said devices in accordance with preset patterns set by said surgeon: and wherein said control means varies the speed of a first surgical device in response to rotation of said foot pedal, and varies the speed of a second instrument when a foot pedal side switch is actuated.

13. An electronic footswitch for use in controlling a plurality of surgical devices having a plurality of operational characteristics within surgeon defined preset patterns of operations when used by a surgeon in ophthalmic surgery, said footswitch comprising:

(a) a supporting member, a shaft and a foot pedal mounted on the shaft for pivotable rotation about a first axis, said shaft being journaled for rotation within the support member:

(b) first and second foot actuable switches mounted at the side of said foot pedal for independent activation of one or more surgical devices throughout the range of motion of said foot pedal:

(c) a spring member mounted about said shaft and coupled to said foot pedal and to said support member to bias said foot pedal to a first predetermined position:

(d) continuously adjustable means for adjusting the bias of said spring member to a surgeon selected value:

(e) electronic encoding means for generating an electronic signal representative of the rotation of said shaft:

(f) control means responsive to said electronic encoding means and said plurality of surgical devices to vary a plurality of operational characteristics of said devices in accordance with preset patterns set by said surgeon: and wherein said control means varies the speed of a first surgical device at a first rate in response to rotation of said foot pedal, and alters the operation of the device when a foot pedal side switch is actuated.

14. An electronic footswitch as claimed in claim 13, wherein at least one or more of the surgical devices has a plurality of a surgeon preset ranges and said apparatus further comprises independent third and fourth foot actuable switches coupled to said control means to enable a surgeon to invoke one or more of said plurality of surgeon preset ranges of said surgical devices.

15. An electronic footswitch as claimed in claim 14, wherein actuation of one of said third or fourth switches alters the surgical instrument controlled by said foot pedal.

16. An electronic footswitch as claimed in claim 11, wherein said spring member is a single coil spring coaxially mounted around said shaft member, said coil spring exerting a preset bias on said foot pedal.

17. An electronic footswitch as claimed in claim 16, wherein said continuously adjustable means is mounted between said frame and said coil spring, and varies the rotational torque exerted by said spring on said shaft.

18. An electronic footswitch for use in controlling a plurality of surgical devices having a plurality of operational characteristics within surgeon defined preset patterns of operations, when used by a surgeon in ophthalmic surgery, said footswitch comprising:

(a) a supporting member, a shaft and a foot pedal mounted on the shaft for pivotable rotation about a first axis said shaft being journaled for rotation within the support member:

(b) first and second side switches mounted on said foot pedal for independent activation of one or more surgical devices throughout the range of motion of said foot pedal;

(c) a spring member mounted about said shaft and coupled to said foot pedal and to said support member to bias said foot pedal to a first predetermined position:

(d) continuously adjustable means for adjusting the bias of said spring member to a surgeon selected value:

(e) electronic encoding means for generating an electronic signal representative of the rotation of said shaft:

(f) control means responsive to said electronic encoding means and said plurality of surgical devices to vary a plurality of operational characteristics of said devices in according with preset patterns set by said surgeon:

(g) wherein said spring member is a single coil spring coaxially mounted around said shaft member said coil spring exerting a preset bias on said foot pedal:

(h) wherein said continuously adjustable means is mounted between said frame and said coil spring, and varies the rotational torque exerted by said spring on said shaft; and wherein said continuously adjustable means includes a rotatable screw member which varies the preload on said coil spring as it is rotated by the surgeon.

19. An electronic footswitch for use in controlling a plurality of surgical devices having a plurality of operational characteristics within surgeon defined preset patterns of operations, when used by a surgeon in ophthalmic surgery, said footswitch comprising:

(a) a supporting member, a shaft and a foot pedal mounted on the shaft for pivotable rotation about a first axis said shaft being journaled for .rotation within the support member:

(b) first and second side switches mounted on said foot pedal for independent activation of one or more surgical devices throughout the range of motion of said foot pedal:

(c) a spring member mounted about said shaft and coupled to said foot pedal and to said support member to bias said foot pedal to a first predetermined position:

(d) continuously adjustable means for adjusting the bias of said spring member to a surgeon selected value:

(e) electronic encoding means for generating an electronic signal representative of the rotation of said shaft:

(f) control means responsive to said electronic encoding means and said plurality of surgical devices to vary a plurality of operational characteristics of said devices in accordance with preset patterns set by said surgeon:

(g) surgeon selectable detent means for providing a tactile feedback to a surgeon as the foot pedal rotates, and wherein said apparatus further comprises a cam member mounted on said shaft, said cam member having a plurality of surfaces thereon which may be engaged by said detent means to provide a tactile feedback to the surgeon.

20. An electronic footswitch as claimed in claim 11, wherein said control means varies the speed of a surgical device when the foot pedal is rotated, and reverses the operation of the device when a foot pedal side switch is actuated.

21. An electronic footswitch for use in controlling a plurality of surgical devices used by a surgeon in ophthalmic surgery, said footswitch comprising:

a frame;

a foot pedal supported by the frame for pivoting rotation with respect to said frame;

a spring member coupled to said foot pedal to bias said foot pedal to resist rotation;

adjustment means coupled to the spring member for adjusting the bias of said spring member at a foot pedal rotational position to a surgeon selected value; and means for generating an electronic signal representative of the rotational position of said shaft.

22. The footswitch as claimed in claim 21 wherein the adjustment means comprises a first gear coupled to the spring member and positioned to flex the spring member upon rotation of the gear, said adjustment means further comprising a manually rotatable worm gear engaging the first gear and causing the first gear to rotate upon rotation of the worm gear.

23. The footswitch as claimed in claim 21, wherein at least one of said surgical devices has a plurality of operating ranges associated therewith, and said apparatus further comprises surgeon selectable detent means for providing a tactile feedback to a surgeon as the foot pedal rotates, said feedback providing an indication of an associated operating range.

24. The footswitch as claimed in claim 21, wherein said apparatus further comprises first and second surgeon actuable foot switches mounted at the sides of said foot pedal, said switches for generating electronic signals representing selections of activating one or more surgical devices.

25. An electronic footswitch as claimed in claim 24, wherein at least one of said surgical devices has a surgeon preset range associated therewith, and said apparatus further comprises at least a third surgeon actuable foot switch for generating an electronic signal representing selection of a preset range by the surgeon for said at least one surgical device.

26. An electronic footswitch as claimed in claim 21, wherein said spring member is a single coil spring coaxially mounted around said shaft, said coil spring exerting a preset bias on said foot pedal.

27. An electronic switch as claimed in claim 26, wherein said adjustment means is mounted between said frame and said coil spring, and varies the rotational torque exerted by said spring on said shaft.

28. An electronic footswitch as claimed in claim 27, wherein said adjustment means includes a rotatable screw member which varies the preload on said coil spring as it is rotated by the surgeon.

29. An electronic footswitch as claimed in claim 23, wherein said apparatus further comprises a cam member mounted on said shaft, said cam member having a plurality of surfaces thereon which may be engaged by said detent means to provide said tactile feedback to the surgeon.

30. An electronic footswitch as claimed in claim 29 wherein said detent means is mounted for reciprocal movement between first and second positions, with said first position in engagement with said cam, and a second position out of engagement with said cam.

* * * * *